US00PP18146P2

(12) United States Plant Patent
Trees

(10) Patent No.: US PP18,146 P2
(45) Date of Patent: Oct. 30, 2007

(54) ***VERBENA* PLANT NAMED 'BALAZMAWITE'**

(50) Latin Name: *Verbena×hybrida*
Varietal Denomination: Balazmawite

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 61 days.

(21) Appl. No.: 11/286,839

(22) Filed: Nov. 22, 2005

(51) Int. Cl.
*A01H 5/00* (2006.01)

(52) U.S. Cl. ..... Plt./308
(58) Field of Classification Search ..... Plt./308
See application file for complete search history.

(56) References Cited

PUBLICATIONS

Abe et al. The Ion–Beam breeding makes Great success in Plant Business +http://epaper.kek.jp/c04/data/CYC2004_papers/19B2.pdf.*
Fehr W.R. Principles of Cultivar development p. 286–303 1987.*
European Plant Breeders' Rights application No. 2004/1606 filed Aug. 30, 2004 and published by the European Community Plant Variety Office (CPVO) on Oct. 15, 2005.

* cited by examiner

*Primary Examiner*—Kent Bell
*Assistant Examiner*—Annette H Para
(74) *Attorney, Agent, or Firm*—Audrey Charles

(57) ABSTRACT

A new and distinct cultivar of *Verbena* plant named 'Balazmawite' characterized by its white-colored flowers, medium green-colored foliage, good basal branching, and vigorous, spreading growth habit.

1 Drawing Sheet

Latin named of genus and species of plant claimed: *Verbena×hybrida*.
Variety denomination: 'Balazmawite'.

BACKGROUND OF THE INVENTION

The present invention relates to a new and distinct cultivar of *Verbena* plant botanically known as *Verbena×hybrida* and hereinafter referred to by the cultivar name 'Balazmawite'.

The new cultivar originated in a controlled breeding program in Illinois during January 2003. The objective of the breeding program was the development of *Verbena* cultivars with unique flower colors and a vigorous trailing, spreading growth habit.

The new cultivar is an irradiation induced sport of 'Balazsilma', U.S. Plant Pat. No. 14,651, characterized by its light violet-colored flowers, compact growth habit, narrow leaf shape, upper leaf surface that is grayed green in color with dark green-colored margins and venation, and lower leaf surface that is grayed purple in color. The irradiation occurred on Jan. 15, 2003. The new cultivar was discovered and selected by the inventor on May 20, 2003 in a controlled environment at Arroyo Grande, Calif.

Asexual reproduction of the new cultivar by terminal stem cuttings since May 2003 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balazmawite' as a new and distinct cultivar of *Verbena* plant:

1. White-colored flowers;
2. Medium green-colored foliage,

3. Good basal branching; and
4. Vigorous, spreading growth habit.

Plants of the cultivar differ from plants of the parent primarily in flower color. Of the many commercially available *Verbena* cultivars known to the inventor, the most similar in comparison to the new cultivar is 'Balazwhit', U.S. Plant Pat. No. 13,943. However, in side by side comparisons, plants of the new cultivar differ from plants of 'Balazwhit' in the following characteristics:

1. Plants of the new cultivar are shorter than plants of 'Balazwhit'; and
2. Plants of the new cultivar have a different flower color from plants of 'Balazwhit'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balazmawite'. The plants were grown 10 cm pots for 13 weeks in a greenhouse at West Chicago, Ill.

DETAILED BOTANICAL DESCRIPTION

Figure 1:
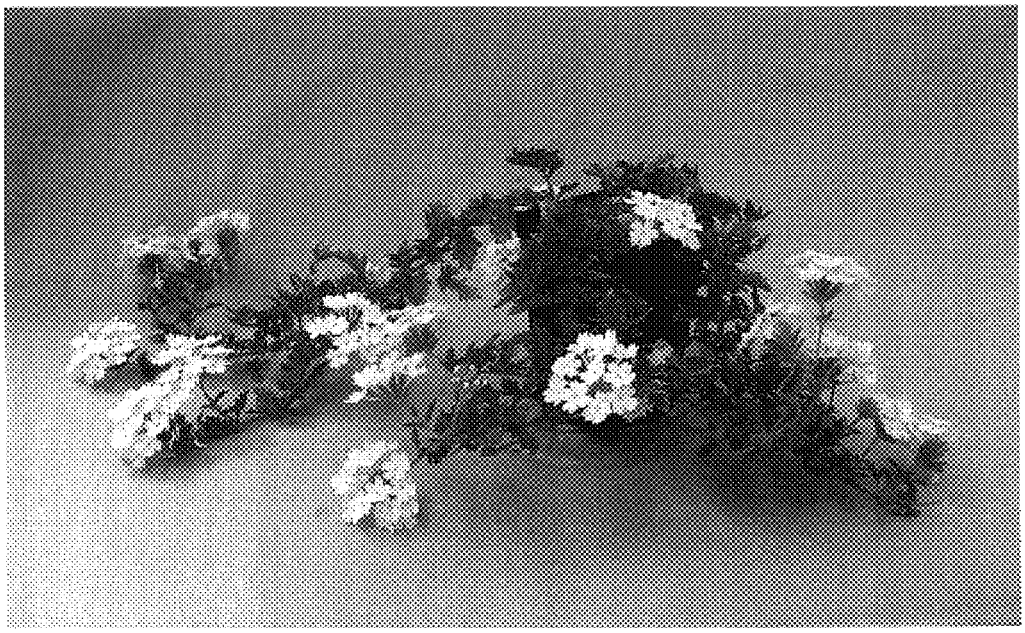
FIG. 1 illustrates a side view of the overall growth and flowering habit of 'Balazmawite'.
Figure 2:
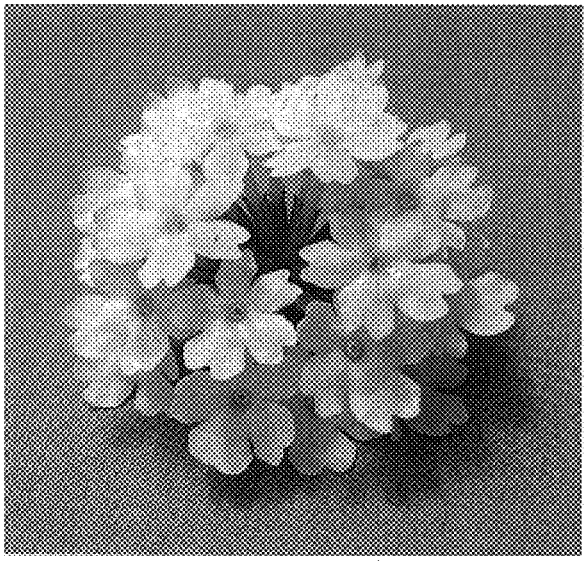
FIG. 2 illustrates a close-up view of a single inflorescence of 'Balazmawite'.
Figure 3:
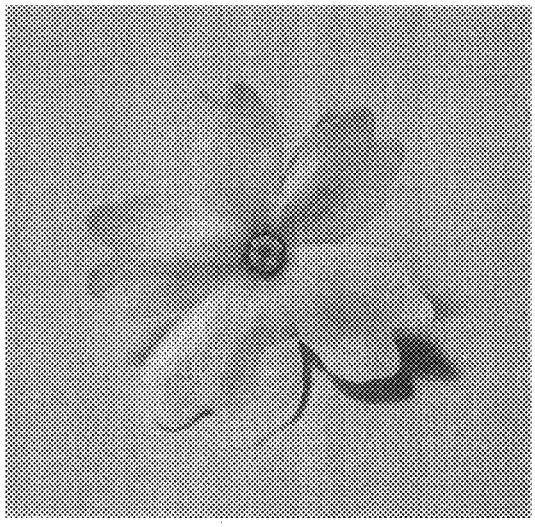
FIG. 3 illustrates a close-up view of a single flower of 'Balazmawite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 25, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 13 weeks utilizing a soilless growth medium. Greenhouse temperatures were maintained at approximately 70° F. to 80° F. (21° C. to 26° C.) during the day and approximately 62° F. to 65° F. (17° C. to 18° C.) during the night. Greenhouse light levels of 5,000 to 8,000 footcandles were maintained during the day.

Botanical classification: *Verbena×hybrida* cultivar Balazmawite.

Parentage: Irradiation induced sport of 'Balazsilma', U.S. Plant Pat. No. 14,641.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Crop time.*—Approximately 5 to 7 weeks from a rooted cutting.

*Growth habit and general appearance.*—Vigorous, spreading.

*Size.*—Height from soil level to top of plant plane: Approximately 5.3 cm. Width: Approximately 58.3 cm.

*Branching habit.*—Freely basal branching. Approximately 6 main branches per plant with lateral branches potentially forming at every node.

*Branch.*—Shape: Square in cross section. Strength: Strong. Length: Approximately 28.3 cm. Diameter: Approximately 2.0 mm. Texture: Hispid. Color: 144A. Internode length at center of branch: Approximately 2.6 cm.

*Foliage.*—Number of leaves per main branch: Approximately 23. Fragrance: None. Form: Simple. Arrangement: Opposite. Aspect: At right angle to stem. Shape: Ovate. Margin: Pinnately cleft. Apex: Acute. Base: Truncate. Venation pattern: Pinnate. Length of mature leaf: Approximately 2.8 cm. Width of mature leaf: Approximately 2.3 cm. Texture of upper and lower surfaces: Densely pubescent with short, soft hairs. Color of upper surface of young and mature foliage: 137A with venation of 145B. Color of lower surface of young and mature foliage: 137C with venation of 145B. Petiole length: Approximately 9.4 mm. Petiole diameter: Approximately 1.5 mm. Petiole texture: Hispid. Petiole color: 145B.

Flowering description:

*Flowering habit.*—'Balazmawite' is freely flowering under outdoor growing conditions with substantially continuous blooming from spring through autumn and year round in greenhouse environment.

*Time to first flower.*—Approximately 10 weeks from sticking of unrooted cutting.

*Lastingness of individual bloom.*—Approximately 5 to 7 days.

Inflorescence description:

*Type.*—Corymb. Quantity per plant: Approximately 8 at 13 weeks. Length/Height: Approximately 3.8 cm. Width: Approximately 5.6 cm. Quantity of fully opened flowers per inflorescence at any one time: Approximately 25.

*Peduncle.*—Strength: Strong. Aspect: Erect. Length: Approximately 3.6 cm. Diameter: Approximately 1.4 mm. Texture: Hirsute. Color: 144A.

Flower description:

*Type.*—Sessile, salverform. Fragrance: None.

*Bud rate of opening.*—Generally takes 3 to 6 days for bud to progress from first color to fully open flower.

*Bud just before opening.*—Shape: Elongated, globular. Length: Approximately 3.4 mm. Diameter: Approximately 3.3 mm. Color: 150D.

*Corolla.*—Shape: Round. Diameter: Approximately 1.7 cm. Depth: Approximately 3.1 mm.

*Petals.*—Quantity: 5 fused at base forming a tube. Appearance: Dull. Aspect: Slightly cupped, becoming flatter with maturity. Shape: Obovate. Apex: Emarginate. Margin: Entire. Texture of upper surface: Glabrous. Texture of lower surface: Puberulent. Length of upper petal from tube: Approximately 7.3 mm. Width of upper petal: Approximately 6.0 mm. Length of lateral petal from tube: Approximately 6.2 mm. Width of lateral petal: Approximately 5.0 mm. Length of lower petal from tube: Approximately 5.9 mm. Width of lower petal: Approximately 3.5 mm. Color of upper surface of all petals when fully open: Closest to 155C with 144C at base. Color of lower surface of all petals when fully open: Closest to 155C. Whiskers closest to 155C surround the opening of the corolla tube.

*Corolla tube.*—Length: Approximately 1.7 cm. Diameter at corolla: Approximately 2.0 mm. Diameter at base: Approximately 1.2 mm. Texture of inner surface: Pubescent. Texture of outer surface: Glabrous except for moderate pubescence at distal end. Color of inner surface: 145D. Color of outer surface: 155D at base and center with 145B at distal end.

*Calyx.*—Shape: Tubular with 5 acute tips. Length/Depth: Approximately 1.0 cm. Width: Approximately 2.4 mm.

*Sepals.*—Quantity per flower: 5. Shape: Linear. Apex: Acute: Margin: Entire. Sepal length: Approximately 1.0 cm. Sepal width: Approximately 1.0 mm. Texture of upper or inner surface: Glabrous. Texture of lower or outer surface: Densely pubescent with a mixture of glandular and non-glandular hairs. Gland color: Colorless, translucent. Color of upper or inner and lower or outer surfaces: 143A. Stipule shape: Lanceolate. Stipule apex: Acuminate. Stipule length: Approximately 6.2 mm. Stipule width at base: Approximately 1.4 mm. Texture of upper or inner surface of stipule: Densely pubescent with a mixture of glandular and non-glandular hairs. Texture of lower or outer surface of stipule: Glabrous. Stipule color: 143A. Gland color: Colorless, translucent.

*Reproductive organs.*—Androecium: Stamen quantity: 4. Stamen length: Approximately 1.0 mm. Anther shape: Ovate, bilobed. Anther length: Approximately 6.0 mm. Anther color: 154A. Pollen amount: None observed. Gynoecium: Pistil quantity: One per flower. Pistil length: Approximately 1.6 cm. Stigma shape: Funnel. Stigma length: Approximately 3.5 mm. Stigma color: 143B. Style length: Approximately 1.2 cm. Style color: 150C. Ovary diameter: Approximately 1.0 mm. Ovary texture: Glabrous. Ovary color: 144B.

Seed and fruit production: Neither seed not fruit production has been observed.

Disease and pest resistance: Resistance to pathogens and pests common to *Verbena* has not been observed.

What is claimed is:

1. A new and distinct cultivar of *Verbena* plant named 'Balazmawite', substantially as herein shown and described.

* * * * *